US00PP29542P3

(12) United States Plant Patent
Snijder

(10) Patent No.: US PP29,542 P3
(45) Date of Patent: Jul. 24, 2018

(54) ***PELARGONIUM* PLANT NAMED 'PEQZ0028'**

(50) Latin Name: *Pelargonium interspecific*
Varietal Denomination: PEQZ0028

(71) Applicant: SYNGENTA PARTICIPATIONS AG, Basel (CH)

(72) Inventor: Ronald Christiaan Snijder, Andijk (NL)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 15/731,628

(22) Filed: Jul. 10, 2017

(65) Prior Publication Data

US 2018/0092277 P1 Mar. 29, 2018

(51) Int. Cl.
*A01H 5/02* (2018.01)

(52) U.S. Cl.
USPC ..... Plt./324
CPC ..... *A01H 5/0277* (2013.01)

(58) Field of Classification Search
USPC ..... Plt./324
See application file for complete search history.

(56) References Cited

PUBLICATIONS

PLUTO Plant Variety Datbase Apr. 9, 2018.*

* cited by examiner

*Primary Examiner* — Annette H Para
(74) *Attorney, Agent, or Firm* — Dale Skalla

(57) ABSTRACT

A new *Pelargonium* plant named 'PEQZ0028' particularly distinguished by the bright red colored and round inflorescences that fade with a slight pink hue held above the medium-green foliage, very heat and drought tolerant with continuous color through the most extreme summer heat, and on a well-branched plant habit.

1 Drawing Sheet

Figure 1:
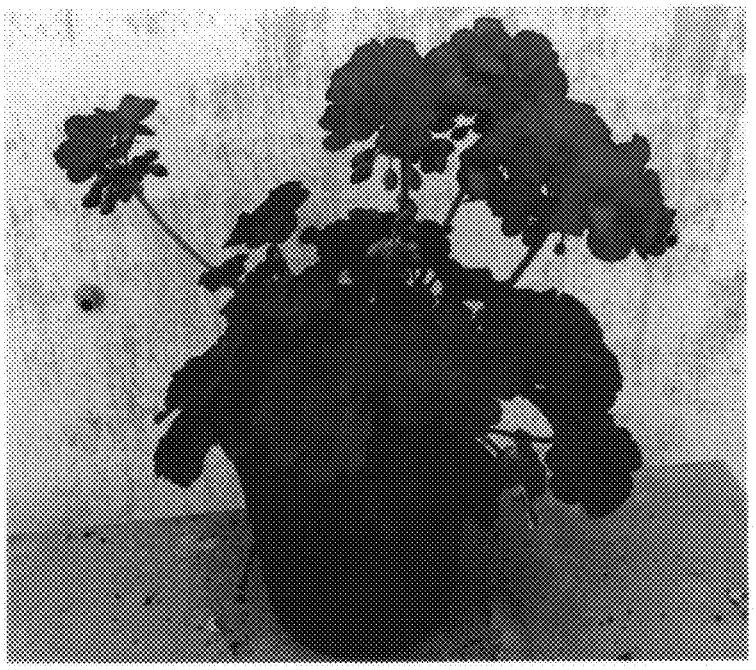

Latin name of the genus and species of the plant claimed: *Pelargonium interspecific.*

Varietal denomination: 'PEQZ0028'.

BACKGROUND OF THE NEW PLANT

The present invention comprises a new *Pelargonium*, botanically known as *Pelargonium interspecific*, and hereinafter referred to by the variety name 'PEQZ0028'.

'PEQZ0028' is a product of a planned breeding program. The new cultivar 'PEQZ0028' has bright red colored inflorescences held above the medium-green foliage, very heat and drought tolerant with continuous color through the most extreme summer heat on a well-branched plant habit.

'PEQZ0028' originates from a hybridization in a controlled breeding program made in April 2010 in a greenhouse in Enkhuizen, The Netherlands. The female parent was an unpatented, proprietary plant of *P. interspecific* parentage, identified as '10664-1' with darker red single florets and larger and more open plant habit when compared to 'PEQZ0028'.

The male parent of 'PEQZ0028' was an unpatented, proprietary plant of *P.×hortorum* parentage, identified as 'k08-4242-1' with more orange red colored florets and a more compact plant habit when compared to 'PEQZ0028'. The resultant seed was sown in December 2010.

'PEQZ0028' was selected as one flowering plant within the progeny of the stated cross in April 2011 in a greenhouse in Enkhuizen, The Netherlands.

The first act of asexual reproduction of 'PEQZ0028'was accomplished when vegetative cuttings were propagated from the initial selection in May 2011 in a greenhouse in Enkhuizen, The Netherlands.

BRIEF SUMMARY OF INVENTION

Horticultural examination of plants grown from cuttings of the plant initiated in May 2011 in Enkhuizen, The Netherlands, and continuing thereafter, has demonstrated that the combination of characteristics as herein disclosed for 'PEQZ0028' are firmly fixed and are retained through successive generations of asexual reproduction.

'PEQZ0028' has not been observed under all possible environmental conditions. The phenotype may vary significantly with variations in environment such as temperature, light intensity, and day length.

Plant Breeder's Rights for this cultivar were applied for in Canada on Apr. 7, 2017, No. 17-9172 and in the European Union on Sep. 28, 2016, No. 2016/2344. 'PEQZ0028' has not been made publicly available prior to the effective filing date of this application, notwithstanding any disclosure that may have been made less than one year prior to the effective filing date of this application by the inventor or another who obtained 'PEQZ0028' directly from the inventor.

The following traits have been repeatedly observed and are determined to be the basic characteristics of the new variety. The combination of these characteristics distinguishes this *Pelargonium* as a new and distinct variety.

BRIEF DESCRIPTION OF THE PHOTOGRAPHS

The accompanying photographic drawing shows typical flower and foliage characteristics of 'PEQZ0028' with colors being as true as possible with an illustration of this type.

Figure 2:
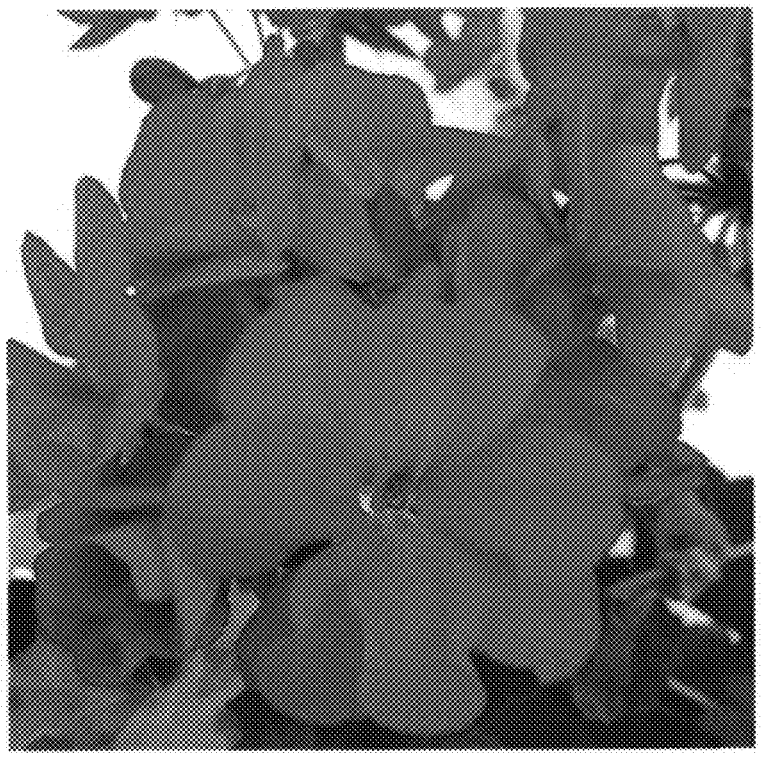

The photographic drawing shows in FIG. 1, a flowering plant of the new variety and in FIG. 2, a close-up of an inflorescence.

DETAILED BOTANICAL DESCRIPTION

The plant descriptions and measurements were taken in Enkhuizen, The Netherlands in late September 2016 under natural light. These plants were 18 weeks old and were grown in a 15 cm pot, in a greenhouse trial. From these plants, one plant is shown on the photographs. The photographs were taken in October 2016.

Color references are made to The Royal Horticultural Society Colour Chart (R.H.S.) 2001.

TABLE 1

DIFFERENCES BETWEEN THE NEW VARIETY 'PEQZ0028' AND A MOST SIMILAR VARIETY

| | 'PEQZ0028' | 'Amri Trared' (U.S. Plant Pat. No. 20,245) |
|---|---|---|
| Anthocyanin coloring of floret pedicel: | Medium to strong | Absent to weak |
| Conspicuousness of marking on upper petal of mature flower: | Weak with some stripes on solid dark red background (RHS 46B) | Medium with stripes on slightly lighter red-purple background (RHS 58B) |
| Color of upper and lower petals: | Rich red color (RHS 46B) | Bright red color (RHS 45B) |

Plant:

*Form, growth and habit.*—Upright, rounded growth habit, heat and drought tolerant with continuous color through the most extreme summer heat, well-branched plant habit.

*Plant height.*—15-17 cm.

*Plant height (inflorescence included).*—21-24 cm.

*Plant width.*—15-20 cm.

Roots:

*Number of days to initiate roots.*—15-18 days at about 22 degrees C.

*Number of days to produce a rooted cutting.*—21-23 days at 22 degrees C.

*Type.*—Fine, fibrous, free branching.

*Color.*—RHS N155B but whiter.

Foliage:

*Immature leaf, color upper surface.*—Closest to RHS 137C.

*Immature leaf, lower surface.*—Closest to RHS 137D.

*Mature leaf, color upper surface.*—Closest to RHS 147B.

*Mature leaf, color lower surface.*—Closest to RHS 148B.

*Length.*—7-7.5 cm.

*Width.*—8-10 cm.

*Shape.*—Cordate.

*Base shape.*—Cordate.

*Apex shape.*—Acute.

*Margin.*—Slightly dentate.

*Texture upper side.*—Hirsute.

*Texture lower side.*—Hirsute.

*Leaf zonation color.*—RHS 147A.

*Color of veins, upper surface.*—RHS 147C becoming indistinct.

*Color of veins, lower surface.*—RHS 145A becoming indistinct.

*Pattern of veining.*—Palmate.

*Petiole color.*—RHS 14BC.

*Petiole length.*—6-9.0 cm.

*Diameter of petiole.*—0.2 cm.

*Texture.*—Pilose, hirsute, glandular hairs.

Stem:

*Quantity of branches.*—5-7.

*Color of stem.*—Between RHS 145A.

*Length of stem.*—4-14 cm.

*Diameter.*—0.4-0.6 cm.

*Length of internodes.*—0.3-2 cm.

*Texture.*—Sparsely hirsute, pilose, glandular hairs.

Peduncle:

*Color of peduncle.*—RHS 147C.

*Length of peduncle.*—12-16 cm.

*Peduncle diameter.*—0.3-0.35 cm.

*Texture.*—Hirsute, glandular hairs.

Pedicel:

*Color of pedicel.*—145A.

*Length of pedicel.*—2.6-3.6 cm.

*Diameter of pedicel.*—0.2-0.3 cm.

*Texture.*—Sparsely pilose, glandular hairs.

Bud (just before opening):

*Color.*—Closest to RHS 46B.

*Length.*—1.5 cm.

*Width.*—0.7-0.8 cm.

*Shape.*—Elliptical.

Inflorescence:

*Type.*—Umbel; semi-spherical or nearly semi-spherical.

*Lastingness of individual flowers.*—7-9 days at 18° C. temperature.

*Number of inflorescences per plant.*—4, with 5 immature umbels in various stages.

*Fragrance.*—None.

*Umbel diameter.*—9-12 cm.

*Umbel depth.*—7-8 cm.

Corolla:

*Form.*—Semi-double.

*Number of petals.*—9-11.

*Diameter of flower.*—About 5.0 cm.

*Depth of flower.*—2-2.5 cm.

*Color upper petals, upper surface.*—RHS 45B.

*Color upper petals, lower surface.*—RHS 46D.

*Length of upper petals.*—2.8 cm.

*Width of upper petals.*—2.2 cm.

*Color lower petals, upper surface.*—RHS 45B.

*Color lower petals, lower surface.*—RHS 45B.

*Length of lower petals.*—2.5 cm.

*Width of lower petals.*—2.3 cm.

*Petal shape.*—Obovate to spathulate.

*Apex shape.*—Rounded.

*Margin.*—Entire.

*Base.*—Attenuate.

*Petal texture.*—Papillose on both surfaces.

Calyx:

*Number of sepals.*—5.

*Color of sepals.*—RHS 144A.

*Length of sepals.*—1.3 cm.

*Width of sepals.*—0.3-0.4 cm.

*Sepal shape.*—Lanceolate to linear.

*Apex shape.*—Acute.

*Margins.*—Mostly fused.

*Texture, upper surface.*—Glabrous.

*Lower surface.*—Glandular hairs, hirsute.

Reproductive organs:
Gynoecium:
*Pistil.*—1.
*Length.*—1.2 cm.
*Style color.*—RHS 43C.
*Style length.*—0.5-0.7 cm.
*Stigma color.*—RHS 42A.
*Ovary color.*—RHS 144D.
*Ovary length.*—0.3-0.4 cm.
*Ovary diameter.*—0.2 cm.
Androecium:
*Number of stamens.*—7.
*Color of filaments.*—RHS 43C at the tip, RHS 155C at the base.
*Length filaments.*—0.7 cm.
*Anther color.*—RHS70A.
*Length of anthers.*—0.2 cm.
*Color of pollen.*—RHS 34C.
*Pollen amount.*—Normal.
*Fertility/seed set.*—Has not been determined to date.
*Disease/pest resistance.*—Has not been determined to date.

What is claimed is:

1. A new and distinct variety of *Pelargonium* plant named 'PEQZ0028' substantially as illustrated and described herein.

* * * * *